United States Patent
Mezera et al.

(10) Patent No.: US 9,732,015 B2
(45) Date of Patent: Aug. 15, 2017

(54) PROCESS FOR THE SELECTIVE HYDROGENATION OF ACETYLENE TO ETHYLENE

(71) Applicant: UOP LLC, Des Plaines, IL (US)

(72) Inventors: Vincent G. Mezera, Brookfield, IL (US); Timur V. Voskoboynikov, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 153 days.

(21) Appl. No.: 14/725,629

(22) Filed: May 29, 2015

(65) Prior Publication Data

US 2016/0347684 A1 Dec. 1, 2016

(51) Int. Cl.
*C07C 5/09* (2006.01)

(52) U.S. Cl.
CPC ........... *C07C 5/09* (2013.01); *C07C 2521/04* (2013.01); *C07C 2523/44* (2013.01); *C07C 2523/50* (2013.01)

(58) Field of Classification Search
CPC combination set(s) only.
See application file for complete search history.

(56) References Cited

U.S. PATENT DOCUMENTS

| | | | |
|---|---|---|---|
| 4,387,263 A | 6/1983 | Vogt et al. | |
| 4,571,442 A | 2/1986 | Cosyns et al. | |
| 7,141,709 B2 | 11/2006 | Cheung et al. | |
| 7,183,451 B2 | 2/2007 | Gattis et al. | |
| 7,208,647 B2 | 4/2007 | Peterson et al. | |
| 7,534,737 B2 | 5/2009 | Gajda | |
| 7,619,125 B2 | 11/2009 | Hori et al. | |
| 7,674,438 B2 | 3/2010 | Cheung et al. | |
| 7,816,571 B2 | 10/2010 | Negiz et al. | |
| 7,919,431 B2 | 4/2011 | Johnson et al. | |
| 8,013,197 B2 | 9/2011 | Peterson et al. | |
| 8,460,937 B2 | 6/2013 | Johnson et al. | |
| 8,471,082 B2 | 6/2013 | Ryu | |
| 8,937,206 B2 | 1/2015 | da Silva Ferreira Alves et al. | |
| 2005/0049445 A1 | 3/2005 | Johnson et al. | |
| 2009/0234167 A1* | 9/2009 | Ryu | C07C 2/78 585/271 |

(Continued)

FOREIGN PATENT DOCUMENTS

| | | |
|---|---|---|
| GB | 871804 A | 6/1961 |
| JP | 2003-236386 A | 8/2003 |

(Continued)

OTHER PUBLICATIONS

Zhou et al. "Solubility of Hydrogen in Pyrolysis Gasoline", J. Chem. Eng. Data, 2006, 51, 972-976, published Mar. 25, 2016.*

(Continued)

*Primary Examiner* — In Suk Bullock
*Assistant Examiner* — Ali Z Fadhel

(57) ABSTRACT

A selective hydrogenation process is described. The process includes dissolving acetylene and hydrogen in a solvent to form a liquid feedstream. The solvent comprises a mixture of a polar organic solvent and a non-polar organic solvent. The liquid feedstream is contacted with a heterogeneous supported selective hydrogenation catalyst at selective hydrogenation conditions to convert at least a portion of the acetylene to ethylene forming a liquid reaction mixture comprising the ethylene produced.

13 Claims, 2 Drawing Sheets

(56) References Cited

U.S. PATENT DOCUMENTS

2012/0209042 A1  8/2012  Mamedov et al.
2014/0058149 A1  2/2014  Negiz et al.

FOREIGN PATENT DOCUMENTS

JP             5177339 B2   4/2013
WO     WO 2012/109085 A1   8/2012

OTHER PUBLICATIONS

Hou et al. "Enhanced Selectivity in the Hydrogenation of Acetylene due to the Addition of a Liquid Phase as a Selective Solvent", I&EC Research, 2013, 52, 13305-13312, published Jul. 9, 2013.*
The International Search Report mailed Sep. 8, 2016 in International Application No. PCT/US2016/032013.

* cited by examiner

PROCESS FOR THE SELECTIVE HYDROGENATION OF ACETYLENE TO ETHYLENE

BACKGROUND OF THE INVENTION

Light olefin materials, including ethylene and propylene, represent a large portion of the worldwide demand in the petrochemical industry. Light olefins are used in the production of numerous chemical products, via polymerization, oligomerization, alkylation and other well-known chemical reactions. These light olefins are essential building blocks for the modern petrochemical and chemical industries for the production of items such as polyethylene. Producing large quantities of light olefin material in an economical manner, therefore, is a focus in the petrochemical industry.

The production of light olefins, and in particular ethylene, can be through steam or catalytic cracking processes. The cracking processes take larger hydrocarbons, such as paraffins, and convert the larger hydrocarbons to smaller hydrocarbons products. The primary product is ethylene. However, there are numerous other chemicals produced in the process. Among the many byproducts are hydrogen, methane, acetylene, and ethane.

Historically, naphtha cracking has provided the largest source of ethylene, followed by ethane and propane pyrolysis, cracking, or dehydrogenation. Due to the large demand for ethylene and other light olefinic materials, however, the cost of these traditional feeds has steadily increased.

Energy consumption is another cost factor impacting the pyrolytic production of chemical products from various feedstocks. Over the past several decades, there have been significant improvements in the efficiency of the pyrolysis process that have reduced the costs of production.

More recent attempts to decrease light olefin production costs include utilizing alternative processes and/or feed streams. In one approach, hydrocarbon oxygenates and more specifically methanol or dimethylether (DME) are used as an alternative feedstock for producing light olefin products. Oxygenates can be produced from available materials such as coal, natural gas, recycled plastics, various carbon waste streams from industry and various products and by-products from the agricultural industry. Making methanol and other oxygenates from these types of raw materials is well established and typically includes one or more generally known processes such as the manufacture of synthesis gas using a nickel or cobalt catalyst in a steam reforming step followed by a methanol synthesis step at relatively high pressure using a copper-based catalyst.

Once oxygenates are formed, the process includes catalytically converting oxygenates, such as methanol, into the desired light olefin products in an oxygenate to olefin (OTO) process. Techniques for converting oxygenates, such as methanol to light olefins (MTO), are described in U.S. Pat. No. 4,387,263, which discloses a process that utilizes a catalytic conversion zone containing a zeolitic type catalyst. This indirect route of production is often associated with energy and cost penalties, often reducing the advantage gained by using a less expensive feed material.

Another alternative process used to produce ethylene involves using pyrolysis to convert natural gas to ethylene. U.S. Pat. No. 7,183,451 discloses heating natural gas to a temperature at which a fraction is converted to hydrogen and a hydrocarbon product such as acetylene or ethylene. The product stream is then quenched to stop further reaction and subsequently reacted in the presence of a catalyst to form liquids to be transported.

A similar process is disclosed in U.S. Pat. No. 7,208,647 in which natural gas is combusted under suitable conditions to convert the natural gas into primarily ethylene and acetylene. The acetylene in the gaseous product stream is separated from the remaining products and converted to ethylene.

More recent efforts have focused on the use of supersonic reactors for the pyrolysis of natural gas into acetylene. For example U.S. Pat. Pub. No. 2014/0058149 discloses a reactor in which a fuel is combusted and accelerated to a supersonic speed. Natural gas is injected into the reactor downstream of the supersonic combustion gas stream, and the natural gas is converted into acetylene as an intermediary product. The reaction is quenched with a liquid to stop the reaction, and the acetylene may be converted to the desired product ethylene in a hydrogenation zone.

Whether an undesired byproduct or one of the desired products, acetylene will irreversibly bond with many downstream catalysts, in particular with polymerization catalysts. Therefore, the production streams which include acetylene must be treated to remove or reduce the amount of acetylene. Additionally, in those processes that produce acetylene as an intermediary product, the majority of the acetylene must be converted to ethylene. One method of converting or reducing the amount of acetylene is selective hydrogenation.

Selective hydrogenation processes can be utilized to reduce the acetylene concentration to a sufficiently low level and can be done in either a gas phase or a liquid phase. Since selective hydrogenation is a highly exothermic reaction, the liquid phase is sometimes preferred as it can better control the temperature of the reaction. For example, U.S. Pat. No. 8,460,937 discloses a process in which acetylene is absorbed into a solvent and passed into a reactor in which a catalyst and hydrogen are present. Under proper reactive conditions, the acetylene is converted into ethylene. The solvent is described as a non-hydrocarbon polar solvent, such as N-methyl-2-pyrrolidone (NMP), dimethylformamide (DMF), acetone, tetrahydrofuran (THF), dimethylsulfoxide (DMSO), and monomethylamine (MMA).

A byproduct of selective hydrogenation is $C_{4+}$ hydrocarbons (hydrocarbons with four or more carbon atoms). The $C_{4+}$ hydrocarbons are undesirable because they can accumulate on catalysts causing coke and fouling the catalyst. Additionally, the creation of the $C_{4+}$ hydrocarbons needlessly consumes the acetylene and can make ethylene separation from the rest of products more complicated.

Therefore, it would be desirable to have a process which reduces the production of the $C_{4+}$ hydrocarbons in a selective hydrogenation of acetylene to ethylene.

It would also be desirable for such a process that is not limited by a specific catalyst.

SUMMARY OF THE INVENTION

One aspect of the invention is a selective hydrogenation process. In one embodiment, the process includes dissolving acetylene and hydrogen in a solvent to form a liquid feedstream. The solvent comprises a mixture of a polar organic solvent and a non-polar organic solvent. The liquid feedstream is contacted with a heterogeneous supported selective hydrogenation catalyst at selective hydrogenation conditions to convert at least a portion of the acetylene to ethylene forming a liquid reaction mixture comprising the ethylene produced.

DETAILED DESCRIPTION OF THE DRAWINGS

DETAILED DESCRIPTION OF THE INVENTION

It has been discovered that for a liquid phase selective hydrogenation of acetylene to ethylene, mixtures of polar solvents and non-polar solvents allow the process to be operated at lower temperatures than with pure N-methyl-2-pyrrolidone, while maintaining high selectivity for ethylene and conversion of acetylene.

The liquid phase acetylene selective hydrogenation process (SHP) utilizes the polar aprotic solvent N-methyl-2-pyrrolidone (NMP), which is a safer alternative to the gas phase acetylene process. However, NMP requires elevated temperature (e.g., greater than about 120° C.) to achieve commercially competitive performance (e.g., 99.5% conversion and about 98% selectivity to ethylene). The ability to operate at lower temperatures while achieving similar performance would result in potentially longer catalyst stability and life, as well as lower operational costs.

It was discovered that the use of a non-polar organic solvent, e.g., p-diethylbenzene (p-DEB), results in an activity advantage allowing operation at lower temperatures. However, p-DEB has much lower solubility for acetylene than NMP. Consequently, the acetylene absorber conditions must be adjusted to higher pressure and/or lower temperature to match the performance in NMP.

Therefore, an improved solvent system was developed that results in higher activities without a loss in performance while maintaining high acetylene and hydrogen solubility by improving the solvent system. For example, the dual solvent system combines a polar organic solvent, such as NMP, with a non-polar organic solvent, such as p-DEB, to gain higher activity and high acetylene and hydrogen solubility. Hydrogen is less soluble than acetylene, particularly in polar solvents. Although not wishing to be bound by theory, the improved activity in the non-polar solvent may be due to better hydrogen availability in the dissolved state. However, hydrogen is not completely soluble at the conditions used; it may form a gas phase in addition to the liquid phase.

Figure 1:
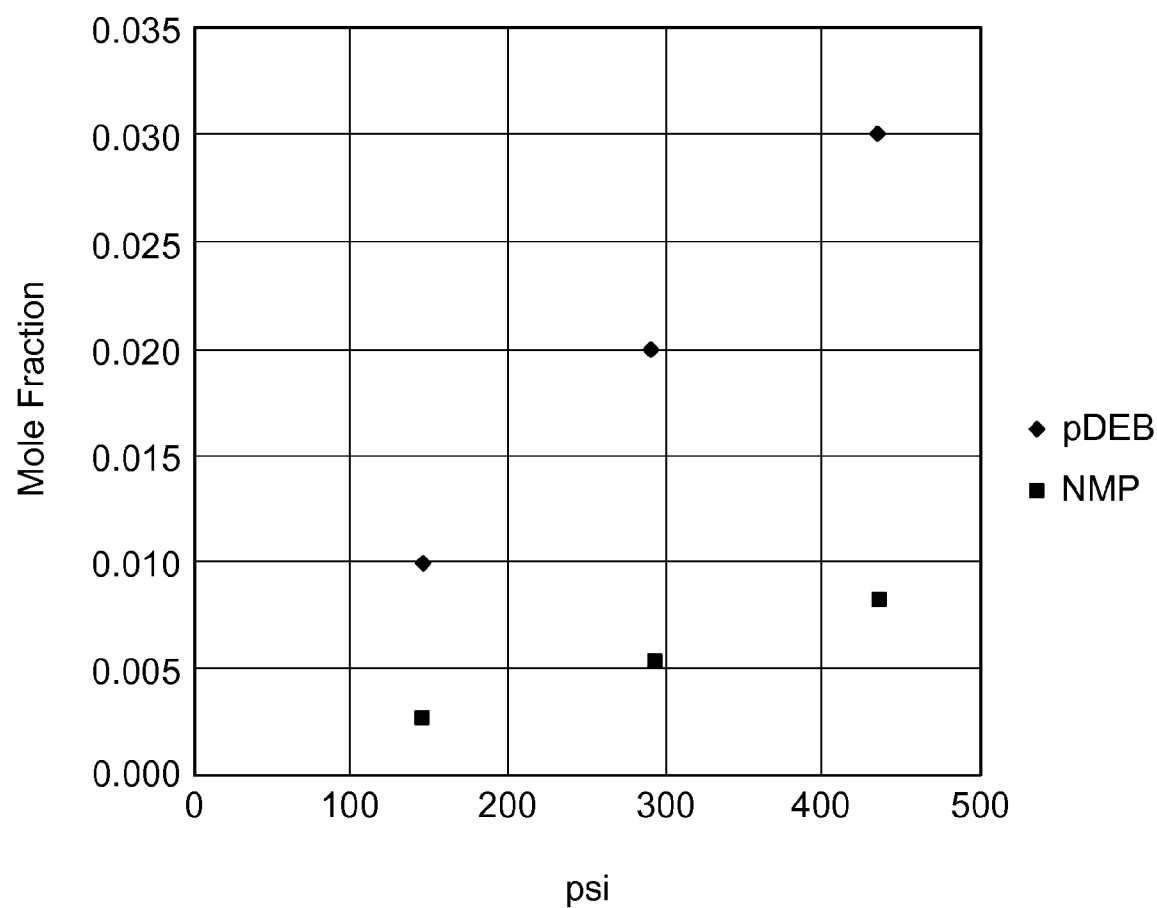
FIG. 1 is a graph illustrating a model of the solubility of hydrogen in N-methyl-2-pyrrolidone and p-diethylbenzene at 150° C.

The improved mixed solvent system results in equivalent or better performance than using a polar aprotic solvent alone. The mixed solvent takes advantage of the higher activity of the non-polar organic solvent while maintaining the acetylene solubility in the polar organic solvent. As a result, the process can be run at lower temperatures saving utility costs and potentially extending catalyst stability and life. Although not wishing to be bound by theory, the improved results may be related to improved hydrogen solubility in non-polar solvents compared to polar ones, for example, as illustrated by the modeled solubility of hydrogen in N-methyl-2-pyrrolidone and p-diethylbenzene at 150° C. shown in FIG. 1.

Figure 2:
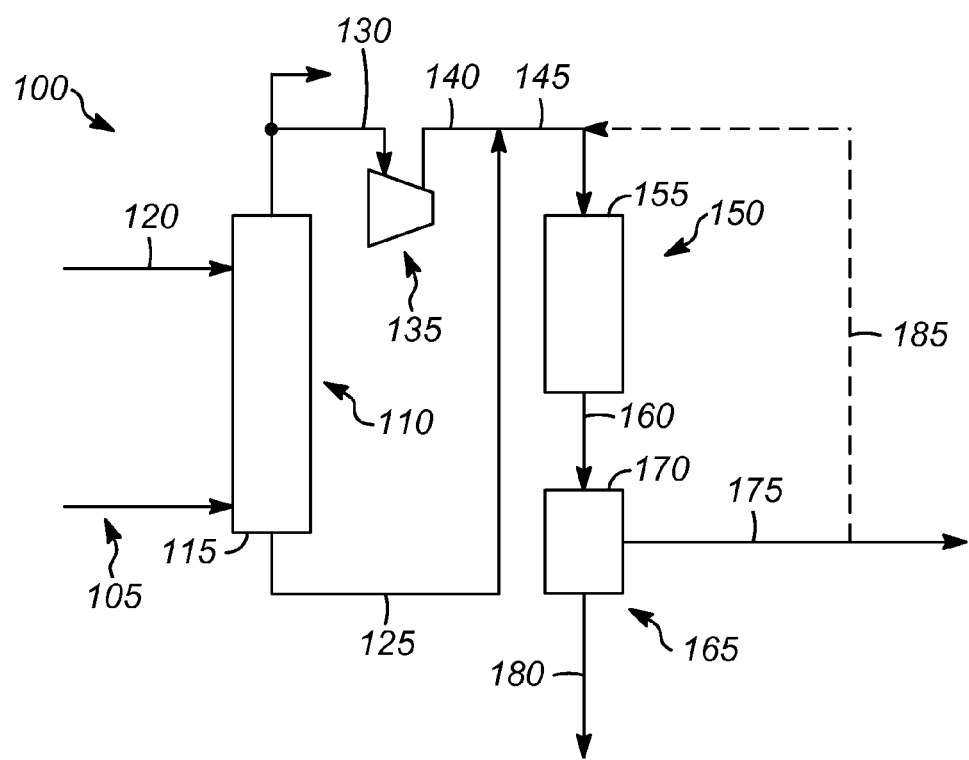
FIG. 2 is a process flow diagram for the liquid phase selective hydrogenation of acetylene to ethylene according to one or more embodiments of the present invention.

FIG. 2 illustrates an exemplary process 100 for a liquid phase selective hydrogenation of acetylene to ethylene in which an acetylene rich vapor steam 105 may be passed to an absorption zone 110. The absorption zone 110 may include one or more absorption columns 115. The acetylene in the stream 105 may be obtained from any industrial process. For example, in some embodiments, the stream 105 may have only a small amount of acetylene which must be treated to remove the acetylene to avoid damaging a downstream polymerization catalyst. In other embodiments, the acetylene rich vapor stream 105 is obtained from a process in which methane is pyrolyzed in a reactor to produce acetylene as an intermediate product, and in some embodiments, the methane is pyrolyzed in a supersonic reactor. In embodiments where acetylene is pyrolyzed to produce ethylene, it is desirable to convert acetylene to ethylene economically and efficiently, and the acetylene conversion must be relatively complete. A second, or downstream conversion can be utilized to polish and remove the remaining trace amounts of acetylene. Thus, in the processes in which the acetylene is the intermediary product and ethylene is the desired product, it is undesirable to convert acetylene to products other than ethylene.

In the absorption zone 110, acetylene in the acetylene rich vapor stream 105 is absorbed into a mixed solvent 120. The mixed solvent 120 contains a polar organic solvent and a non-polar organic solvent. Suitable polar organic solvents are those with high acetylene solubility, including, but not limited to, N-methyl-2-pyrrolidone, dimethylformamide, acetone, tetrahydrofuran, dimethylsulfoxide, and monomethylamine, acetonitrile, or combinations thereof. Among these solvents, the ones with higher boiling point and low chemical reactivity are preferred. The most preferred polar solvent is N-methyl-2-pyrrolidone. The non-polar organic solvent is chemically inert and has a boiling point of at least about 100° C., or at least about 120° C., or at least about 140° C. Suitable non-polar organic solvents include, but are not limited, to, monoalkyl substituted aromatics, dialkyl substituted aromatics, trialkyl substituted aromatics, and paraffins with 8 or more carbon atoms and chemically inert. By "chemically inert" it is meant that the solvents, both polar and non-polar, do not react under process conditions with each other, nor do they react with either the feed or the products of selective hydrogenation: acetylene, hydrogen, CO, and ethylene. Examples of suitable non-polar organic solvents include, but are not limited to, diethylbenzenes, (e.g., p-diethylbenzene, m-diethylbenzene, o-diethylbenzene), xylenes (p-xylene, m-xylene, o-xylene), cumene, mesitylene, decane, dodecane, or combinations thereof. In one embodiment, the polar organic solvent is N-methyl-2-pyrrolidone, and the non-polar organic solvent is p-diethylbenzene, The polar organic solvent can be present in amounts of about 90 vol % to about 10 vol % and about 10 vol % to about 90 vol % of the non-polar organic solvent, or about 85 vol % to about 15 vol % polar organic solvent and about 15 vol % to about 85 vol % of the non-polar organic solvent, or about 80 vol % to about 20 vol % and about 20 vol % to about 80 vol % of the non-polar organic solvent. The exact ratio of polar to non-polar solvent may depend on process economics and may vary between commercial units; each of them is unique due to variance of the feedstock and product price, utilities and labor costs, etc. If higher activity is preferred, then this ratio is higher, and if the higher selectivity is more important, then this ratio is lower.

The concentration of acetylene in the solvent mixture is desirably less than 5 wt %, or between 0.1% to about 5% by weight, between about 0.1% to about 3% by weight, or between about 1% to about 2% by weight, or between about 0.5% to about 5% by weight, or between about 0.5% to about 3% by weight, or between about 0.5% to about 2% by weight, or between about 1% to about 5% by weight, or between about 1% to about 3% by weight.

A first stream 125 being a liquid and comprising solvent and dissolved acetylene is removed from the absorption zone 110. A second stream 130 being an acetylene lean vapor stream and comprising at least hydrogen gas is also removed from the absorption zone 110. In order to allow downstream reactors to operate at higher pressures, the second stream 130 (or a portion thereof) may be passed to a compression zone 135 to provide a compressed second stream 140.

The compressed second stream 140 and the first stream 125 from the absorption zone 110 may be combined into a combined stream 145 which is passed to a hydrogenation zone 150. Alternatively, the compressed second stream 140 and the first stream 125 can be introduced into the hydrogenation zone 150 separately. Carbon monoxide may also be passed to the hydrogenation zone 150. While the second stream 130 from the absorption zone 110 may include carbon monoxide, carbon monoxide can also be recovered from a downstream reaction effluent stream or carbon monoxide may be added to the process from another source. The hydrogen and other gases supplied to hydrogenation zone 150 in stream 130 may be supplemented by any suitable source of for example purified hydrogen or carbon monoxide. The concentration of carbon monoxide in stream 130 may vary depending on the source of the acetylene rich stream 105 entering absorption zone 110. In an embodiment, the carbon monoxide concentration will be in the range of about 1 to about 50 mol %, or about 5 to about 35 mol %, or about 5 to about 20 mol %.

The hydrogenation zone 150 may include at least one hydrogenation reactor 155. Each hydrogenation reactor 155 includes a hydrogenation catalyst, typically a hydrogenation metal in an amount between 0.01 to 5.0 wt % on a support, wherein the hydrogenation metal is preferably selected from a Group VIII metal. Preferably, the metal is palladium (Pd), platinum (Pt), nickel (Ni), rhodium (Rh), or a mixture thereof. More preferably, a Group VIII metal is modified by one or more metals, selected from Group IB through IVA, such as zinc (Zn), indium (In), tin (Sn), lead (Pb), copper (Cu), silver (Ag), gold (Au) in an amount between 0.01 and 5 wt %. Preferred supports are aluminum oxides (aluminas), pure or doped with other metal oxides, synthetic or natural (i.e. clays). More preferred supports are alpha-aluminas of various shape and size (i.e. spheres, extrudates), with high degree of conversion to alpha phase.

In the hydrogenation reactor 155, in the presence of the catalyst, under hydrogenation conditions, the hydrogen reacts with the acetylene to produce ethylene. The hydrogen may be in the second stream 130 from the absorption zone 110, or hydrogen may come from a portion of a downstream reaction effluent, or hydrogen may be added to the process.

Typical hydrogenation reaction conditions in the hydrogenation reactor 155 include a temperature that may range between about 50° C. and about 250° C., or between about 50° C. and about 200° C., or between about 50° C. and about 160° C., or between about 70° C. and about 250° C., or between about 70° C. and about 200° C., or between about 70° C. and about 160° C. Additionally, the hydrogenation reactor 155 is operated at a high pressure which may range between approximately 0.69 MPa (100 psig) and about 3.4 MPa (500 psig), preferably between approximately 1.0 MPa (150 psig) and about 2.8 MPa (400 psig). The liquid hour space velocity (LHSV) at the reactor inlet of the hydrogenation reaction can range between about 1 and about 100 $h^{-1}$, with preferred ranges being between about 5 and about 50 $h^{-1}$, between about 5 and about 25 $h^{-1}$, and between about 5 and about 15 $h^{-1}$.

The acetylene reacts with the hydrogen present to form ethylene. The reactor effluent stream 160, which contains the hydrogenation reaction products, is passed to a separation zone 165 which contains, for example, a separator vessel 170.

In the separator vessel 170 of the separation zone 165, the reaction effluents are separated into an overhead vapor stream 175 and a bottoms liquid stream 180. The separation may be obtained using any suitable separation process, including, but not limited to, reducing the pressure in the separator vessel 170, and/or increasing the temperature of the separator vessel 170. The majority of the ethylene will separate from the liquid phase even when the conditions are not changed due to the decreased solubility of ethylene in the solvent.

The separation zone 165 can be a separation vessel from the hydrogenation zone 150, or the separation zone 165 and the hydrogenation zone 150 can be the same vessel.

The overhead vapor stream 175 is rich in ethylene and may contain other gases. The further processing of the overhead vapor stream 175 and the bottoms liquid stream 180 is not necessary for an understanding and practicing of the present invention. However, since the overhead vapor stream 175 may include carbon monoxide and hydrogen, a portion 185 of this stream 175 may be recycled back to the combined stream 145 entering the hydrogenation zone 150 to provide carbon monoxide and hydrogen for the hydrogenation reactions. Alternatively, portion 185 can be mixed with either the compressed second stream 140 or the first stream 125, or it the can be introduced into the hydrogenation zone 150 separately.

The selectivity for ethylene for the process using the mixed solvent is at least about 95%, or at least about 96%, or at least about 97%, or at least about 98%. The selectivity is calculated by taking the ratio of ethylene weight, to the sum of weights of ethylene and all other products, including ethane, $C_4$ hydrocarbons, and oxygen-containing hydrocarbons, in %. The latter are believed to be formed upon reaction between hydrocarbons and CO.

The conversion of acetylene is at least about 95%, or at least about 96%, or at least about 97%, or at least about 98%, or at least about 99%, or at least about 99.5%. Conversion is calculated by taking the ratio: (weight of acetylene fed less weight of acetylene unconverted)/weight of acetylene fed, in %.

EXAMPLES

The selective hydrogenation catalyst was 0.35% Pd-0.64% Ag, supported on Alpha-Alumina spheres. It was activated (reduced) by treating with hydrogen at 400° C. for 1 hr.

The selective hydrogenation process was run using a pure NMP solvent and a solvent mixture containing 80 vol % NMP and 20 vol % p-DEB. The feedstock contained about 1.8-2.0 wt % acetylene in the solvent, either pure or mixed. The temperature, liquid hourly space velocity, hydrogen to acetylene molar ratio, and hydrogen to carbon monoxide molar ratio for the runs are shown in Table 1. The pressure was 1.8 MPa (250 psig).

The data shows that, at the same acetylene/solvent concentration (maintained at 1.8-2.0 wt % acetylene), the acetylene conversion reaches the same level (about 99.2%, and about 99.8%) at a temperature 10° C. lower in mixed p-DEB/NMP than in pure NMP, while high selectivity to ethylene was maintained. In other words, the same temperature conversion in mixed p-DEB/NMP is higher than in pure NMP. Without being bound to any specifics, on the basis of our experience it is believed that a 10° C. difference in temperature is equivalent to at least 10% difference in acetylene conversion.

Although not wishing to be bound by theory, the fact that the $C_2$ selectivity is a little higher and the $C_{4+}$ selectivity is a little lower may support the suggestion that the origin of the increased activity in p-DEB is $H_2$ availability at the surface of the catalyst as a result of improved $H_2$ solubility in non-polar media. However, the increase in selectivity could also be a result of the slightly higher ratio of hydrogen to acetylene.

TABLE 1

| R# | Solvent | LHSV hr$^{-1}$ | Molar ratios | | T, °C. | Conv. wt % | Selectivity, wt % | | | | | |
|---|---|---|---|---|---|---|---|---|---|---|---|---|
| | | | H$_2$:C$_2$H$_2$ | H$_2$:CO | | | C$_{2-}$ | C$_2$ | C$_4$ | C$_3$ Oxy | C$_{6+}$ | Σ of C$_{4+}$ |
| 1 | 100NMP | 10 | 9 | 10 | 120.7 | 99.15 | 98.06 | 0.22 | 1.3 | 0.3 | 0.1 | 1.45 |
| 2 | | 10 | 9 | 10 | 129.4 | 99.79 | 98.05 | 0.33 | 1.1 | 0.3 | 0.2 | 1.28 |
| 3 | 80NMP- | 10 | ~10 | 10 | 110.2 | 99.23 | 98.01 | 0.47 | 0.9 | 0.5 | 0.1 | 0.99 |
| 4 | 20PDEB | 10 | ~10 | 10 | 119.5 | 99.86 | 97.43 | 0.79 | 1.0 | 0.7 | 0.1 | 1.12 |

As used herein, the term about means within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed:

1. A selective hydrogenation process comprising:
   dissolving acetylene and hydrogen in a solvent to form a liquid feedstream, the solvent comprising a mixture of N-methyl-2-pyrrolidone (NMP) and p-diethylbenzene; and
   contacting the liquid feedstream with a heterogeneous supported selective hydrogenation catalyst at selective hydrogenation conditions to convert at least a portion of the acetylene to ethylene forming a liquid reaction mixture comprising the ethylene produced.

2. The process of claim 1 further comprising separating the ethylene produced from the liquid reaction mixture.

3. The process of claim 2 wherein separating the ethylene produced from the liquid reaction mixture comprises at least one of reducing the pressure, and increasing the temperature.

4. The process of claim 1 wherein the solvent comprises about 90 vol % to about 10 vol % of N-methyl-2-pyrrolidone and about 10 vol % to about 90 vol % of p-diethylbenzene.

5. The process of claim 1 wherein the selectivity for ethylene is at least about 97%.

6. The process of claim 1 wherein the conversion of acetylene is at least about 99%.

7. The process of claim 1 wherein the selective hydrogenation conditions include at least one of: a temperature in a range of about 50° C. to about 250° C., and a pressure of about 0.69 MPa to about 3.4 MPa.

8. The process of claim 1 wherein the solvent comprises about 90 vol % to about 10 vol % of the polar organic solvent and about 10 vol % to about 90 vol % of the non-polar organic solvent.

9. A selective hydrogenation process comprising:
   dissolving acetylene and hydrogen in a solvent to form a liquid feedstream, the solvent comprising a mixture of N-methyl-2-pyrrolidone (NMP) and p-diethylbenzene;
   contacting the liquid feedstream with a heterogeneous supported selective hydrogenation catalyst at selective hydrogenation conditions to convert at least a portion of the acetylene to ethylene forming a liquid reaction mixture comprising the ethylene produced; and
   separating the ethylene produced from the liquid reaction mixture.

10. The process of claim 9 wherein separating the ethylene produced from the liquid reaction mixture comprises at least one of reducing the pressure, and increasing the temperature.

11. The process of claim 9 wherein the solvent comprises about 90 vol % to about 10 vol % of N-methyl-2-pyrrolidone and about 10 vol % to about 90 vol % of p-diethylbenzene.

12. The process of claim 9 wherein the selectivity is at least about 97%, or wherein the conversion is at least about 99%, or both.

13. The process of claim 9 wherein the selective hydrogenation conditions include a temperature in a range of about 50° C. to about 250° C., and a pressure of about 0.69 MPa to about 3.4 MPa.

* * * * *